(12) United States Patent
Kondo et al.

(10) Patent No.: US 9,049,036 B2
(45) Date of Patent: Jun. 2, 2015

(54) COMPUTER SYSTEM ANALYZING APPARATUS AND COMPUTER SYSTEM ANALYZING METHOD

(75) Inventors: Takashi Kondo, Otawara (JP); Kenichi Niwa, Otawara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 1618 days.

(21) Appl. No.: 11/071,187

(22) Filed: Mar. 4, 2005

(65) Prior Publication Data

US 2005/0222992 A1  Oct. 6, 2005

(30) Foreign Application Priority Data

Mar. 5, 2004 (JP) ................................. 2004-062040
Feb. 9, 2005 (JP) ................................. 2005-033186

(51) Int. Cl.
| G09G 5/00 | (2006.01) |
| H04L 12/24 | (2006.01) |
| H04L 12/26 | (2006.01) |
| H04L 29/08 | (2006.01) |
| H04L 29/14 | (2006.01) |
| G06F 19/00 | (2011.01) |

(52) U.S. Cl.
CPC ............ *H04L 12/24* (2013.01); *G06F 19/3412* (2013.01); *H04L 41/00* (2013.01); *H04L 41/147* (2013.01); *H04L 43/0817* (2013.01); *H04L 67/12* (2013.01); *H04L 69/40* (2013.01)

(58) Field of Classification Search
USPC ............................................................ 707/3
See application file for complete search history.

(56) References Cited

U.S. PATENT DOCUMENTS

| 5,420,605 | A | * | 5/1995 | Vouri et al. ................... 345/698 |
| 5,459,837 | A | * | 10/1995 | Caccavale ..................... 709/226 |
| 5,555,376 | A | * | 9/1996 | Theimer et al. ............... 709/229 |
| 5,635,952 | A | * | 6/1997 | Gable ........................... 345/698 |
| 5,675,510 | A | * | 10/1997 | Coffey et al. ................. 709/224 |
| 5,678,041 | A | * | 10/1997 | Baker et al. ...................... 707/9 |
| 5,682,529 | A | * | 10/1997 | Hendry et al. ................ 713/100 |
| 5,740,801 | A | * | 4/1998 | Branson ........................ 600/407 |
| 5,799,318 | A | * | 8/1998 | Cardinal et al. ............. 707/101 |
| 6,028,585 | A | * | 2/2000 | Ishii et al. ..................... 345/581 |
| 6,076,166 | A | * | 6/2000 | Moshfeghi et al. ............... 726/4 |
| 6,119,186 | A | * | 9/2000 | Watts et al. ................... 710/104 |
| 6,148,335 | A | * | 11/2000 | Haggard et al. ............. 709/224 |
| 6,178,443 | B1 | * | 1/2001 | Lin ............................... 709/208 |
| 6,226,407 | B1 | * | 5/2001 | Zabih et al. .................. 382/209 |
| 6,230,204 | B1 | * | 5/2001 | Fleming, III ................. 709/229 |
| 6,260,021 | B1 | * | 7/2001 | Wong et al. ....................... 705/2 |
| 6,282,701 | B1 | * | 8/2001 | Wygodny et al. ............. 717/125 |

(Continued)

FOREIGN PATENT DOCUMENTS

| JP | 6-214962 | 8/1994 |
| JP | 8-227404 | 9/1996 |

(Continued)

*Primary Examiner* — Augustine K Obisesan
(74) *Attorney, Agent, or Firm* — Oblon, McClelland, Maier & Neustadt, L.L.P.

(57) ABSTRACT

A computer system analyzing apparatus includes an acquiring unit which acquires information indicating at least use states of a plurality of computer resources, and a detecting unit which detects whether each of the use states of the computer resources which are indicated by the information corresponds to a state determined as an unreasonable state in advance.

3 Claims, 16 Drawing Sheets

(56) References Cited

U.S. PATENT DOCUMENTS

| | | | |
|---|---|---|---|
| 6,313,833 B1* | 11/2001 | Knight | 705/36 R |
| 6,327,623 B2* | 12/2001 | Watts | 709/229 |
| 6,411,836 B1* | 6/2002 | Patel et al. | 600/407 |
| 6,452,692 B1* | 9/2002 | Yacoub | 358/1.15 |
| 6,489,936 B1* | 12/2002 | Gormish | 345/2.1 |
| 6,520,912 B1* | 2/2003 | Brooks et al. | 600/437 |
| 6,556,724 B1* | 4/2003 | Chang et al. | 382/299 |
| 6,671,802 B1* | 12/2003 | Ott | 713/100 |
| 6,724,733 B1* | 4/2004 | Schuba et al. | 370/252 |
| 6,907,607 B1* | 6/2005 | Mummert et al. | 718/104 |
| 6,996,610 B2* | 2/2006 | Bantz et al. | 709/220 |
| 7,051,095 B1* | 5/2006 | Cantwell | 709/223 |
| 7,092,987 B2* | 8/2006 | Brittingham et al. | 709/203 |
| 2002/0082864 A1* | 6/2002 | Kelley et al. | 705/2 |
| 2002/0112052 A1* | 8/2002 | Brittingham et al. | 709/224 |
| 2002/0140974 A1 | 10/2002 | Imaizumi et al. | |
| 2003/0002748 A1* | 1/2003 | Funahashi | 382/274 |
| 2003/0053810 A1* | 3/2003 | Jackelen et al. | 399/16 |
| 2003/0084091 A1* | 5/2003 | Agarwalla et al. | 709/203 |
| 2003/0093503 A1* | 5/2003 | Yamaki et al. | 709/220 |
| 2003/0191509 A1* | 10/2003 | Flynn et al. | 607/60 |
| 2003/0233252 A1* | 12/2003 | Haskell et al. | 705/2 |
| 2004/0064037 A1* | 4/2004 | Smith | 600/420 |
| 2004/0083291 A1* | 4/2004 | Pessi et al. | 709/227 |
| 2004/0122703 A1* | 6/2004 | Walker et al. | 705/2 |
| 2004/0174320 A1* | 9/2004 | Matthijs et al. | 345/30 |
| 2004/0215490 A1* | 10/2004 | Duchon et al. | 705/2 |
| 2004/0254763 A1* | 12/2004 | Sakai et al. | 702/184 |
| 2004/0267891 A1* | 12/2004 | Hoeye et al. | 709/206 |
| 2005/0066011 A1* | 3/2005 | Wicks | 709/217 |
| 2005/0068252 A1* | 3/2005 | Driver et al. | 345/1.1 |
| 2005/0107689 A1* | 5/2005 | Sasano | 600/425 |
| 2005/0110953 A1* | 5/2005 | Castaldi et al. | 353/30 |
| 2005/0125440 A1* | 6/2005 | Hirst | 707/103 R |

FOREIGN PATENT DOCUMENTS

| | | |
|---|---|---|
| JP | 2001-94744 | 4/2001 |
| JP | 2001-216506 | 8/2001 |
| JP | 2003-58520 | 2/2003 |

\* cited by examiner

| MAC ADDRESS | IP ADDRESS | DEVICE | PLACE 1 | PLACE 2 | PLACE 3 |
|---|---|---|---|---|---|
| ********** | .......... | ROUTER S | EAST BUILDING | 1F | |
| ********** | .......... | ROUTER A | EAST BUILDING | 2F | |
| ********** | .......... | ROUTER B | EAST BUILDING | 3F | |
| ********** | .......... | ROUTER C | WEST BUILDING | 1F | |
| ********** | .......... | ROUTER D | WEST BUILDING | 2F | |
| ********** | .......... | HUB A | WEST BUILDING | 2F | |
| ********** | .......... | CLIENT VIEWER A | EAST BUILDING | 2F | ROOM A |
| ********** | .......... | CLIENT VIEWER B | EAST BUILDING | 3F | ROOM B |
| ********** | .......... | CLIENT VIEWER C | WEST BUILDING | 1F | ROOM C |
| ********** | .......... | CLIENT VIEWER D | WEST BUILDING | 2F | ROOM D |
| ********** | .......... | CLIENT VIEWER E | WEST BUILDING | 3F | ROOM E |

FIG. 3

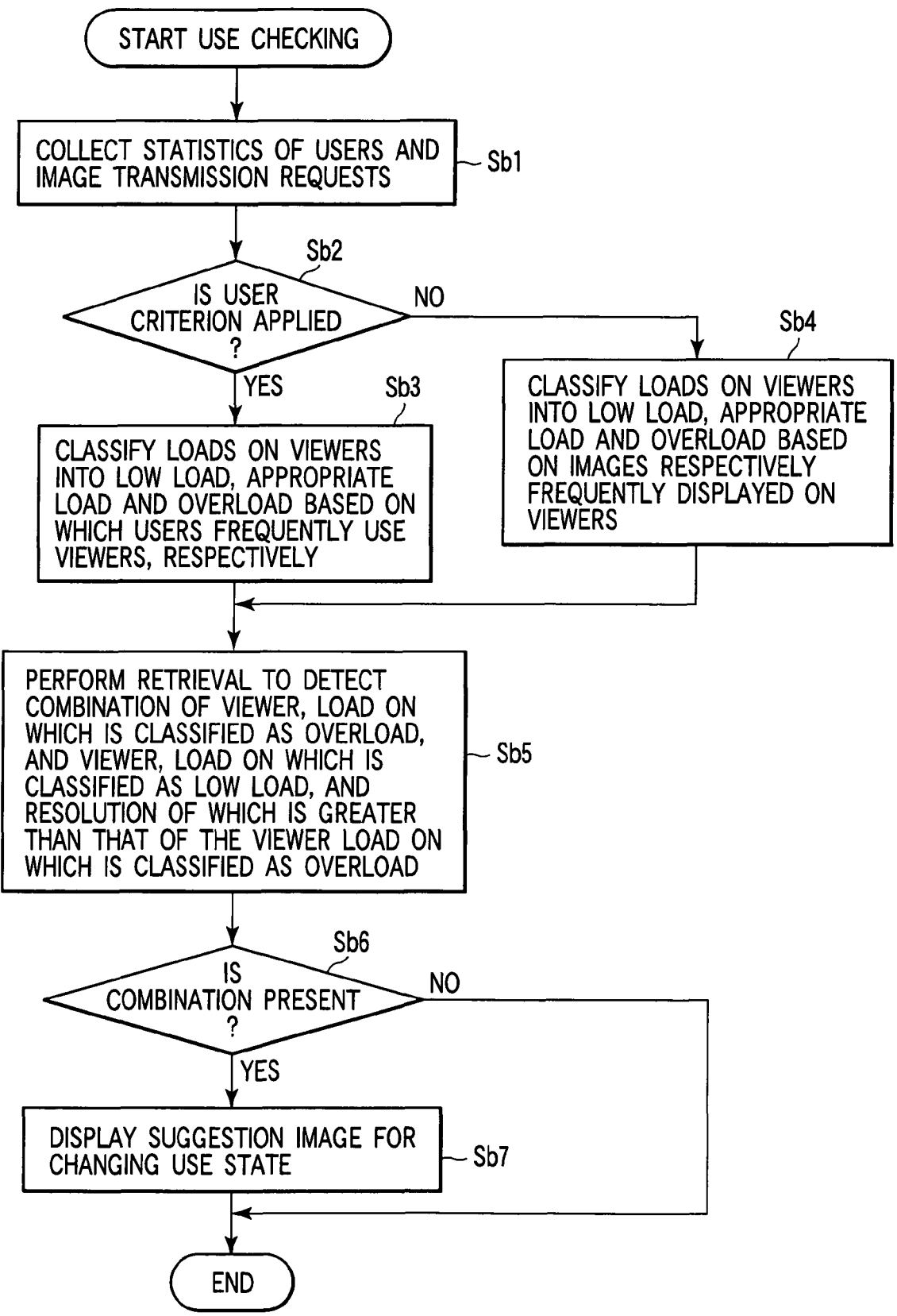
F I G. 6

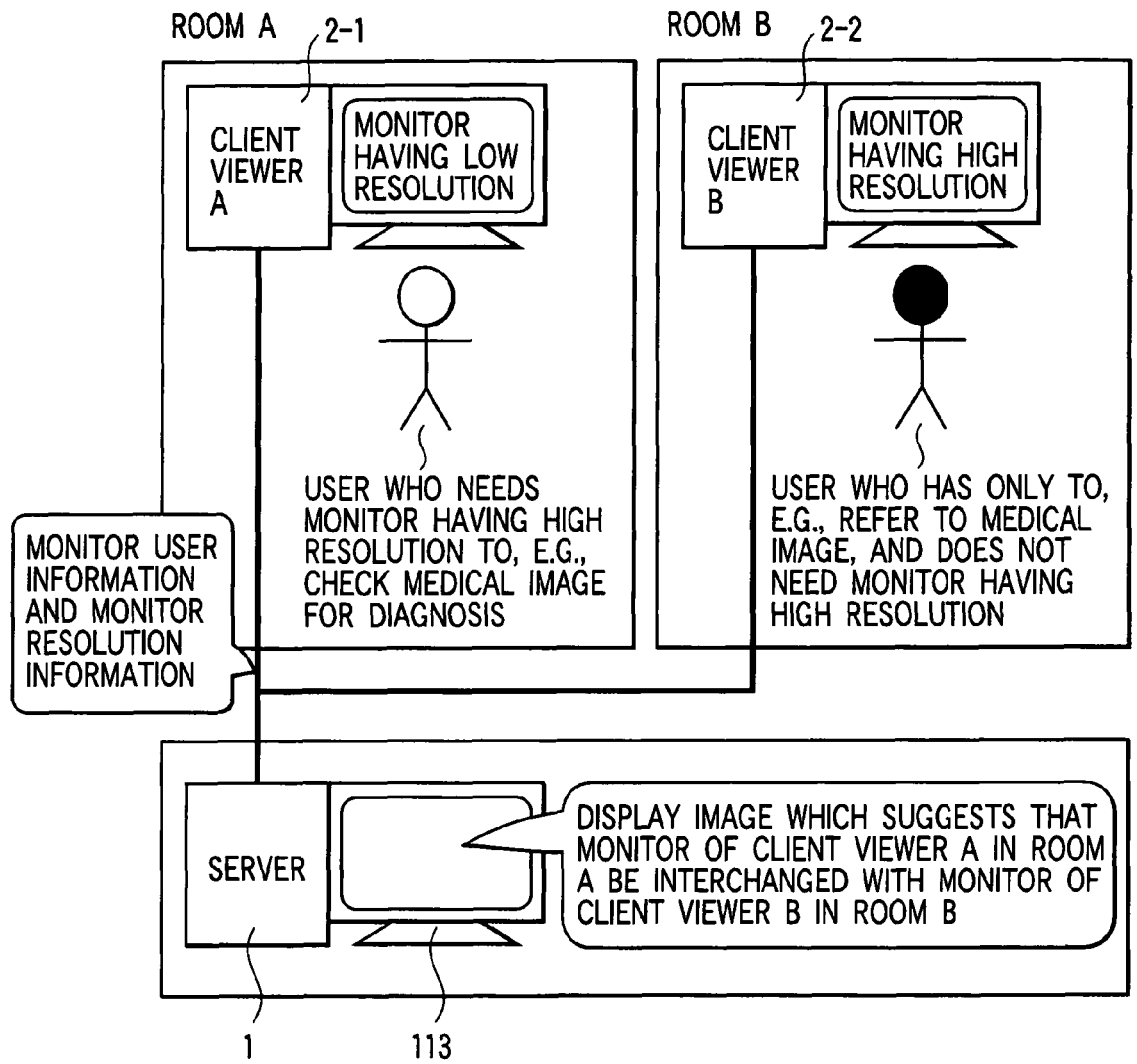
F I G. 7

| TYPE OF MONITOR | TYPE OF OCCUPATION | | |
|---|---|---|---|
| | DOCTOR | NURSE | OTHER |
| HIGH-RESOLUTION MONITOR | O | | |
| INTERMEDIATE-RESOLUTION MONITOR | O | O | |
| LOW-RESOLUTION MONITOR | | O | O |

| | RESOLUTION (×3) | FREQUENCY OF USE (×2) | DISTANCE (×1) | TOTAL SCORE |
|---|---|---|---|---|
| VIEWER X1 | 9 | 1 | 5 | 34 |
| VIEWER X2 | 9 | 5 | 5 | 42 |
| VIEWER X3 | 5 | 9 | 5 | 38 |
| VIEWER Y1 | 5 | 5 | 9 | 34 |
| VIEWER Y2 | 5 | 5 | 9 | 34 |
| VIEWER Y3 | 1 | 5 | 9 | 22 |

COMPUTER SYSTEM ANALYZING APPARATUS AND COMPUTER SYSTEM ANALYZING METHOD

CROSS-REFERENCE TO RELATED APPLICATIONS

This application is based upon and claims the benefit of priority from prior Japanese Patent Applications No. 2004-062040, filed Mar. 5, 2004; and No. 2005-033186, filed Feb. 9, 2005, the entire contents of both of which are incorporated herein by reference.

BACKGROUND OF THE INVENTION

1. Field of the Invention

The present invention relates to a computer system analyzing apparatus and a computer system analyzing method, both for checking whether a computer system such as a medical image observing system has a problem or not.

2. Description of the Related Art

A medical image observing system using a computer system is well known (as disclosed in, e.g., Jpn. Pat. Appln. KOKAI Publication No. 2001-94744). In such a medical image observing system, image data obtained by an examination apparatus (modality) is stored in an image server. The image data stored in the image server is read out therefrom by a client viewer via a network, and is then displayed as a medical image by the client viewer. Thus, when deciding or confirming how to treat a patient, a doctor or a nurse can refer to the medical image displayed on the client viewer.

Such computer systems do not necessarily have computer resources of the highest capability. To be more specific, as often happens, there is a case where even when a number of computer resources of the same type are used in a computer system, they have different capabilities or different functions due to various restrictions. For example, a display having a high resolution is used as a client viewer for a doctor, but one having a lower resolution is used as a client viewer for a nurse.

Up to now, a user or a system designer might consider and study how computer resources should be arranged to establish a computer system. However, actually, it has been difficult for a user to establish an optimal computer system in consideration of the functions of individual computer resources, etc., and much labor is required to do so. In addition, even if an optimal computer system is established, there is a case where the optimization is lost when the application purpose is changed.

BRIEF SUMMARY OF THE INVENTION

The present invention has been made in consideration of the above circumstances, its object being to perform the checking necessary to optimize a computer system.

According to a first aspect of the present invention, there is provided a computer system analyzing apparatus comprising: an acquiring unit which acquires information indicating at least use states of a plurality of computer resources; and a detecting unit which detects whether each of the use states of the computer resources which are indicated by the information corresponds to a state determined as an unreasonable state in advance.

According to a second aspect of the present invention, there is provided a computer system analyzing method comprising: acquiring information indicating at least use states of a plurality of computer resources; and detecting whether each of the use states of the computer resources which are indicated by the information corresponds to a state determined as an unreasonable state in advance.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a view showing the data structure of location information stored in a location information storage section in FIG. 2.

FIG. 6 is a flowchart of use checking.

FIG. 7 is a view showing an example of an unreasonable state detected in the use checking.

DETAILED DESCRIPTION OF THE INVENTION

The embodiments of the present invention will be explained with reference to the accompanying drawings.

First Embodiment

Figure 1:
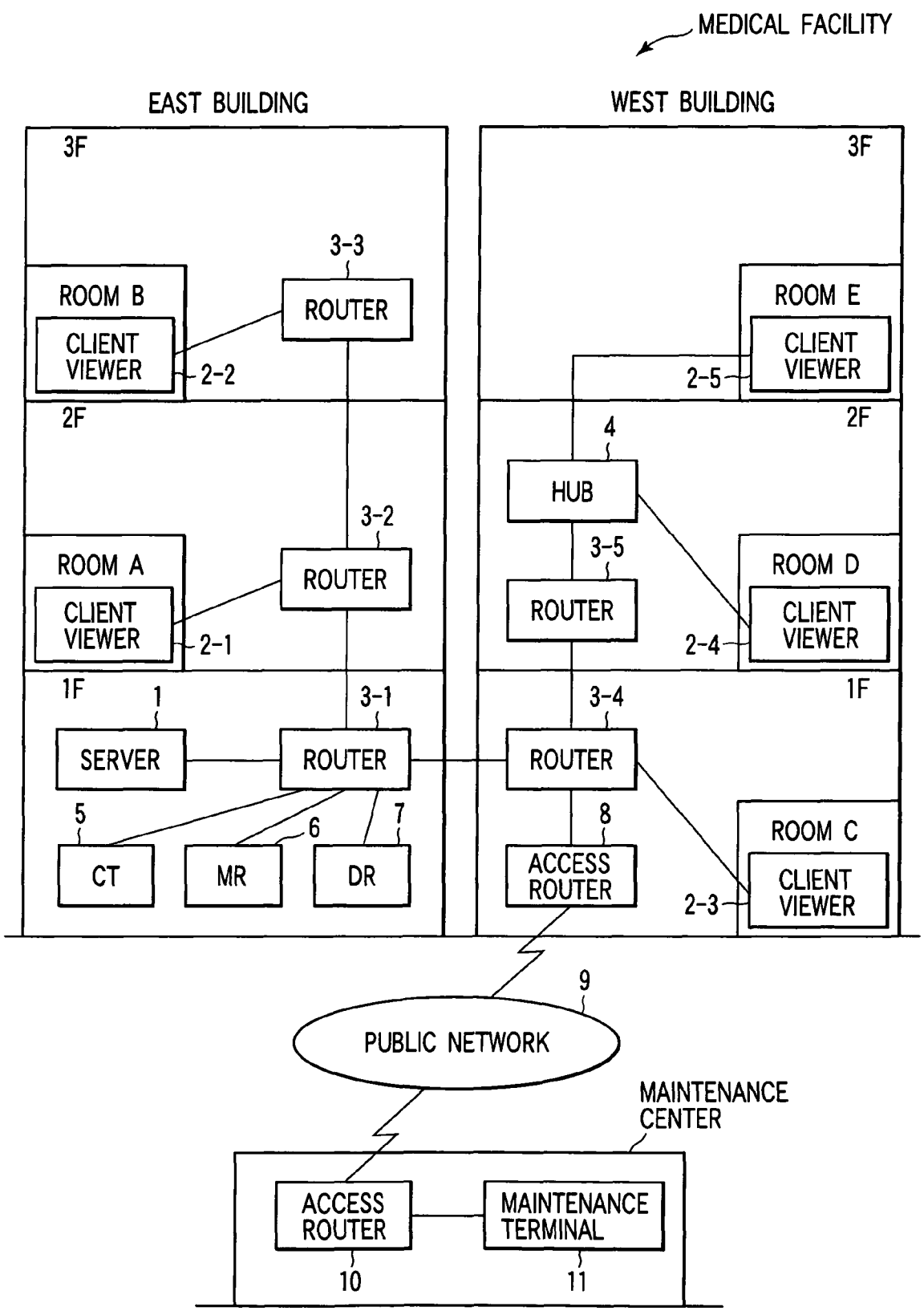
FIG. 1 is a block diagram showing the entire structure of a medical image observing system to which a computer system analyzing apparatus according to a first embodiment of the present invention is applied.

FIG. 1 is a block diagram showing the entire structure of a medical image observing system to which a computer system analyzing apparatus according to a first embodiment of the present invention is applied. This medical image observing system is introduced into a medical facility comprising an east building of three stories and a west building of three stories.

On the first floor of the east building, a server 1 is provided. In the medical facility, a number of client viewers 2 are provided. To be more specific, client viewers 2-1 to 2-5 are provided in rooms A to E, respectively, which are located on the second and third floors of the east building and the first to third floors of the west building, respectively. It should be noted that when the client viewers need to be distinguished from each other, they will be referred to as "client viewer 2-1", "client viewer 2-2", . . . , as appropriate; however, when they do not need to be distinguished from each other, they will be each referred to as "client viewer 2".

The server 1 and the client viewers 2 can communicate with each other via a local area network (LAN) including routers 3-1 to 3-5 and a hub 4. On the first floor of the east building, a computed tomography (CT) scanner 5, a magnetic resonance (MR) apparatus 6 and a digital radiography (DR) apparatus 7, etc. are provided as examination apparatuses, and are connected to the LAN through the router 3-1.

On the first floor of the west building, an access router 8 is provided. The access router 8 is connected to a public network 9. Furthermore, the access router 8 can communicate with an access router 10 provided in a maintenance center via the public network 9. To the access router 10, a maintenance terminal 11 is connected, and from the maintenance terminal 11, the LAN of the medical facility can be accessed via the public network 9 and the access router 8.

In the medical image observing system, medical image data generated by the CT scanner 5, the MR apparatus 6 and the DR apparatus 7 is collected and stored in the server 1. A user such as a doctor or a nurse can gain access to the server 1 by using the client viewer 2, and arbitrarily make a monitor of the client viewer 2 display a medical image.

Figure 2:
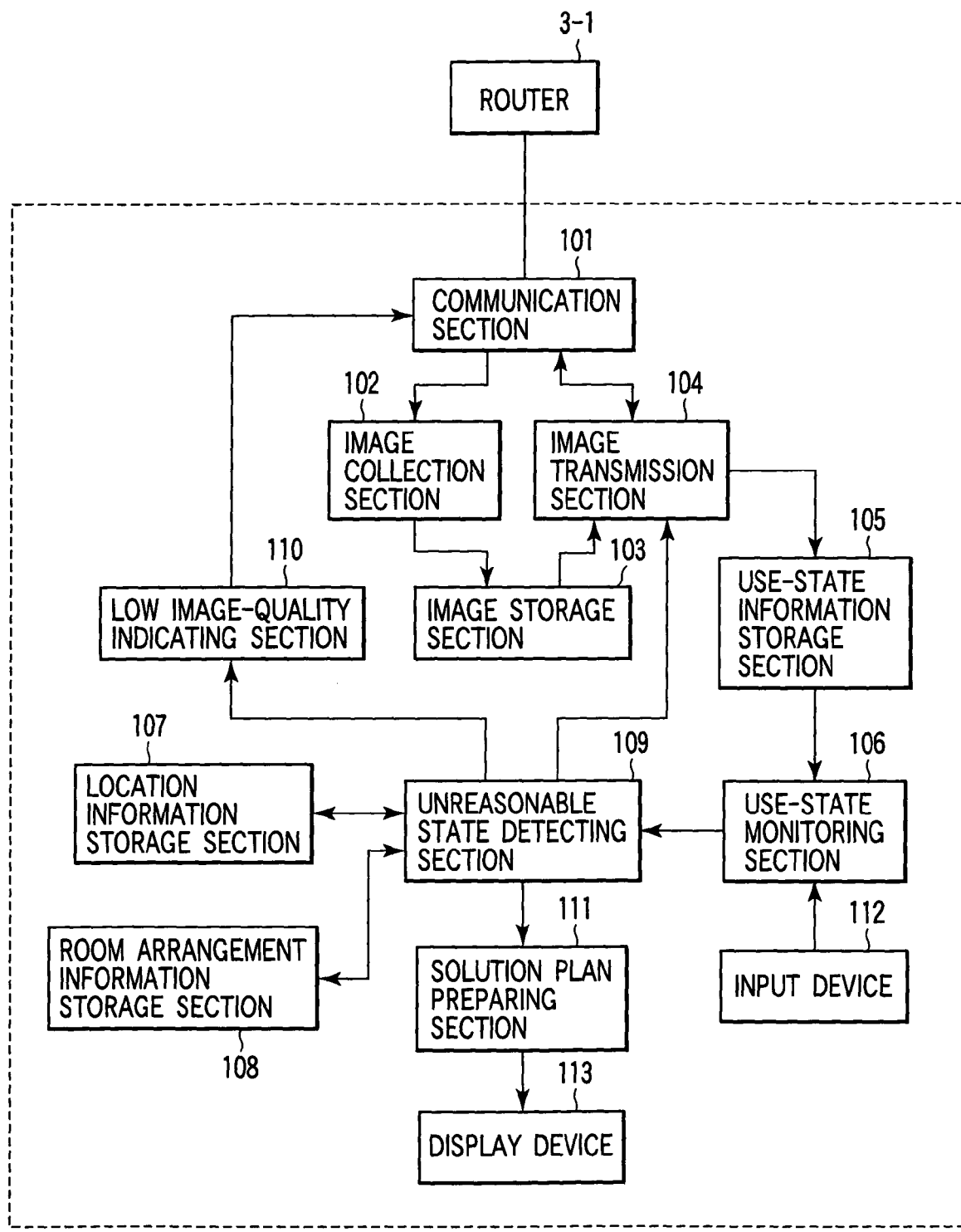
FIG. 2 is a block diagram showing the structure of the server in FIG. 1.

FIG. 2 is a block diagram showing the structure of the server 1 in FIG. 1.

As shown in FIG. 2, the server 1 comprises a communication section 101, an image collection section 102, an image storage section 103, an image transmission section 104, a use-state information storage section 105, a use-state monitoring section 106, a location information storage section 107, a room arrangement information storage section 108, an unreasonable state detecting section 109, a low image-quality indicating section 110, a solution plan preparing section 111, an input device 112 and a display device 113.

The server 1 can use a general-purpose computer apparatus as a basic hardware. It should be noted that when a processor incorporated in the computer apparatus is made to execute a program, it can serve as the image collection section 102, the image transmission section 104, the use state monitoring section 106, the unreasonable state detecting section 109, the low image-quality indicating section 110 and the solution plan preparing section 111. In this case, the computer apparatus on which the above program is installed can serve as the server 1. The program may be installed on the computer apparatus in advance. Alternatively, the program may be recorded on a removable recording medium such as a CD-ROM or be delivered to the computer apparatus via a network, and then be installed on the computer apparatus. Furthermore, the image storage section 103, the use-state information storage section 105, the location information storage section 107 and the room arrangement information storage section 108 can be formed of storage devices such as memories provided in the computer apparatus or a hard disk therein, an external storage device such as an external memory or an external hard disk which is added to the computer apparatus, and a removable recording medium such as an optical disk.

The communication section 101 is connected to the router 3-1, and performs communication through the router 3-1. The image collection section 102 collects medical image data generated by the CT scanner 5, the MR apparatus 6 and the DR apparatus 7 via the LAN. Also, the image collection section 102 causes the collected medical image data to be stored in the image storage section 103. The image transmission section 104 transmits the medical image data stored in the image storage section 103 in response to an image transmission request which is made by a client viewer 2. Also, when being accessed by the client viewer 2, the image transmission section 104 receives apparatus information and user information which are information regarding the client viewer 2 and information regarding the user of the client viewer 2, respectively. The apparatus information indicates the specification of a CPU provided in the client viewer 2, the capacity of a memory in the client viewer 2 and the resolution of a monitor therein. The user information indicates the name and occupation of the user. The image transmission section 104 stores the received apparatus information, user information and image transmission request, in the user-state information storage section 105. The user-state monitoring section 106 acquires the apparatus information, the user information and the image transmission request, from the user-state information storage section 105, and monitors the user state of the client viewer 2 based on those information.

The location information storage section 107 stores location information, which is information indicating the MAC address, the IP address, the device name and the place with respect to the routers 3-1 to 3-5 and the hub 4 as shown in, e.g., FIG. 3. It should be noted that the entire location information may be prepared by an administrator or the like. Alternatively, the server 1 may have a function of automatically preparing part of the location information. For example, since information regarding the routers 3-1 to 3-5 and the hub 4 is obtained at the time of establishing the LAN, it can be added to the location information. If it is added, the "place 1" and "place 2" of each of the client viewers 2, which are shown in FIG. 3, can be automatically estimated from the places where the routers and hub connected to the client viewers 2 are located. However, when a client viewer 2 is placed on a floor different from a floor on which a router or hub connected to the client viewer 2 is placed, as in the client viewer 2-5, it is necessary to manually input the "place 1" and "place 2" of the client viewer 2. Also, the "place 3" thereof, which is shown in FIG. 3, needs to be manually input.

Figure 4:
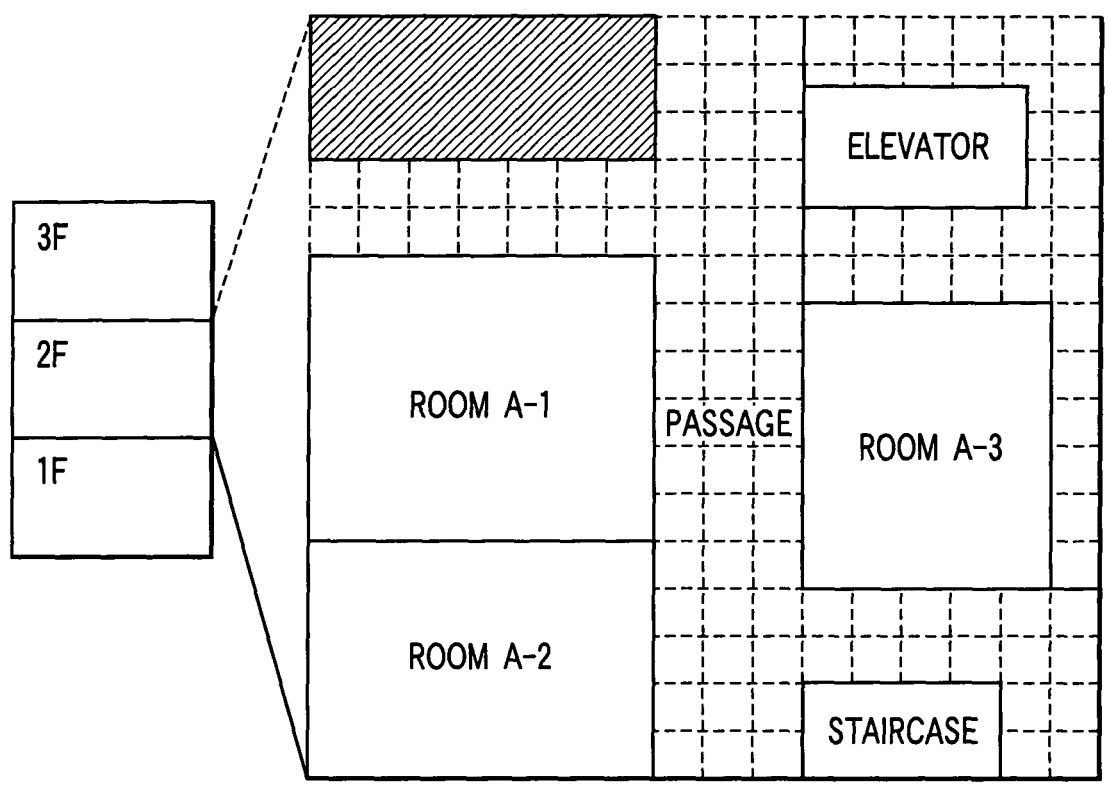
FIG. 4 is a view showing an example of a floor plan indicated by room arrangement information stored in a room arrangement storage section in FIG. 2.

The room arrangement information storage section 108 stores room arrangement information, which is information indicating such a floor plan as shown in, e.g., FIG. 4, which shows the room arrangement of each of the floors of the medical facility. If the server 1 is provided to have a function of easily preparing a floor plan, i.e., it can automatically prepare it, or a floor plan can be acquired as electronic data, the floor plan can be utilized as the room arrangement information.

The unreasonable state detecting section 109 detects whether the use state of a client viewer 2 is in an unreasonable state or not on the basis of the result of monitoring by the use-state monitoring section 106, the location information and the room arrangement information. The unreasonable state to be detected by the unreasonable state detecting section 109 is classified into the following four states: (1) a state in which the resolution of the monitor of a client viewer 2 which is now used by a user, and makes a request for medical image data is lower than that of a client viewer 2 which the above user usually uses (this state will be referred to as a first unreasonable state); (2) a state in which a client viewer 2 (which will be referred to as an overloaded client viewer 2) which frequently displays a medical image with high definition with respect to the resolution of its monitor and a client viewer 2 (which will be referred to as a low loaded client viewer 2) which frequently displays a medical image with low definition with respect to the resolution of its monitor, or which is not frequency used are both present, and the resolution of the monitor of the low loaded client viewer 2 is greater than that of the monitor of the overloaded client viewer 2 (this state will be referred to as a second unreasonable state); (3) a state in which the frequencies of use of client viewers 2 which are used by a number of users are unbalanced (this state will be referred to as a third unreasonable state); and (4) a state in which when a user uses a client viewer 2 which is separated from a main place for the user, which will be described later, by a predetermined distance or more, another client viewer 2 is present which is located closer to the main place than the above client viewer 2, and which satisfies a use condition required by the user (this state will be referred to a fourth unreasonable state).

When the unreasonable state detecting section 109 detects the first unreasonable state, the low image-quality indicating section 110 sends low image-quality indicating information to a client viewer 2 in order that a notice indicating that the image quality is low be displayed on the client viewer 2. When the unreasonable state detection section 109 detects any of the second to fourth unreasonable states, the solution plan preparing section 111 prepares a plan for solving a problem included in the detected reasonable state.

The input device 112 comprises, for example, a keyboard or a mouse, etc. The input device 112 accepts an instruction for executing checking of any of the second to fourth unreasonable states. As the display device 113, e.g., a liquid crystal display can be applied. The display device 113 displays the solution plan prepared by the solution plan preparing section 111.

The operation of the medical image observing system having the above structure will be explained mainly with respect to the operation of the server 1.

Figure 5:
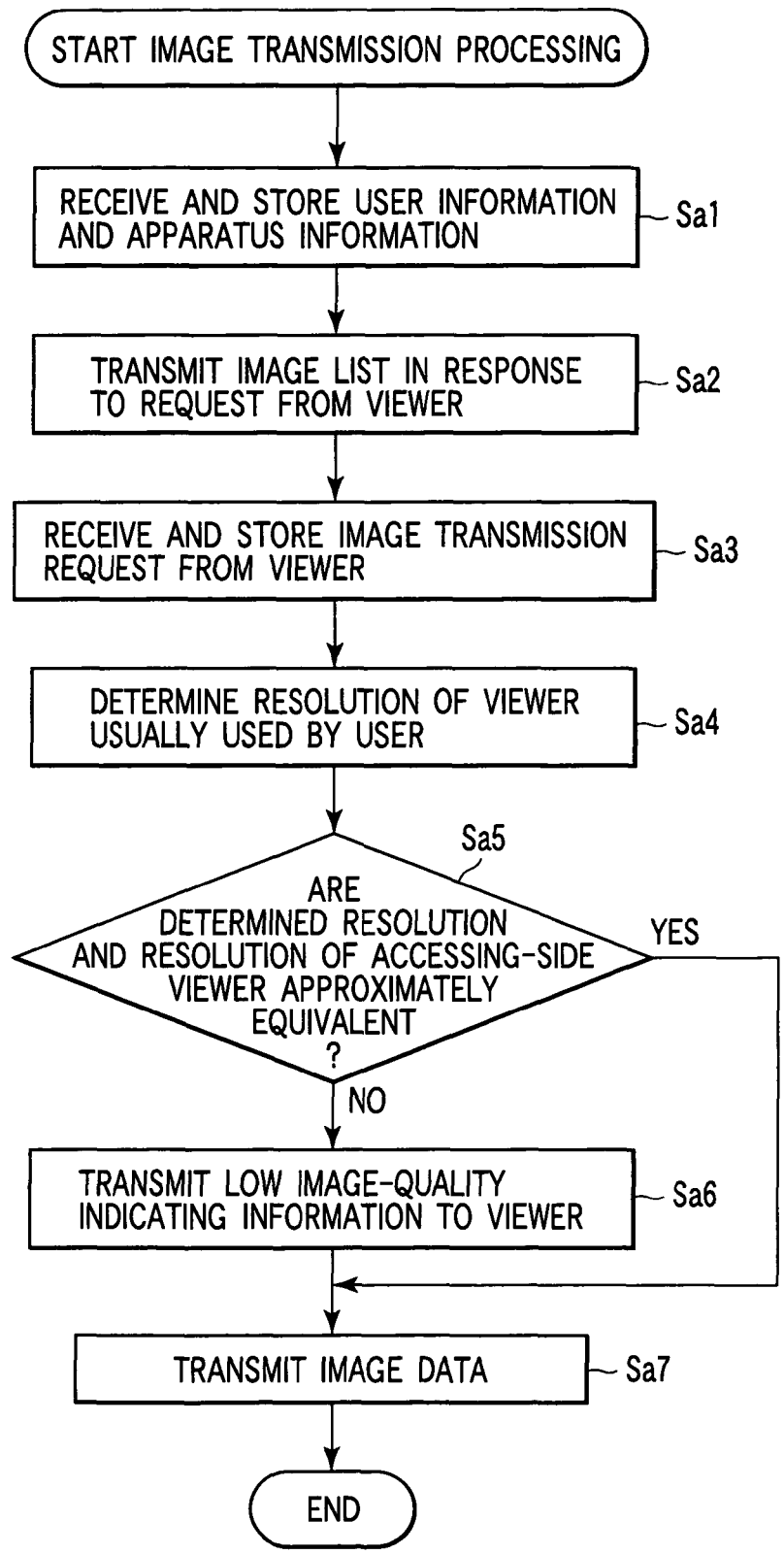
FIG. 5 is a flowchart of image transmission processing.

When a user such as a doctor or a nurse wishes to observe a medical image, he or she gets access to the server 1 by using a client viewer 2. In this case, in the server 1, an image transmission processing, which is shown in FIG. 5, is executed by the image transmission section 104, the use-state monitoring section 106, the unreasonable state detecting section 109 and the low image-quality indicating section 110. Of the client viewers 2, the above client viewer 2 used to get access to the server 1 will be referred to as an accessing-side client viewer 2.

In a step Sa1, the image transmission section 104 receives user information and apparatus information from the accessing-side client viewer 2, and stores those information in the use-state information storage section 105. In a step Sa2, the image transmission section 104 transmits a list of medical image data stored in the image storage section 103 to the accessing-side client viewer 2 in response to a request therefrom. In a step Sa3, the image transmission section 104 receives an image transmission request which is sent from the accessing-side client viewer 2 based on the above list, and stores the image transmission request in the use-state information storage section 105 such that the request is associated with the user information and the apparatus information. In such a manner, since the user information, the apparatus information and the image transmission request are stored in association with each other in the use-state information storage section 105, it can be determined from those information which medical image has been observed (to be more specific, for instance, which part of a living body has been imaged as an image, and which modality has been applied), which user has observed it, and which client viewer 2 has been used to observe it.

In a step Sa4, the user-state monitoring section 106 analyzes the information stored in the use-state information storage section 105, to thereby determine the resolution of the monitor of a client viewer 2 which is usually used by a user which now uses the accessing-side client viewer 2. In a step Sa5, the use-state monitoring section 106 determines whether the above determined resolution and the resolution of the accessing-side client viewer 2 are approximately equivalent or not.

When it is determined in the step Sa5 that they are not, the step to be carried out proceeds from the step Sa5 to the step Sa6. In the step Sa6, the low image-quality indicating section 110 transmits the low image-quality indicating information to the accessing-side client viewer 2. The low image-quality indicating information is information to be displayed by the accessing-side client viewer 2. When the low image-quality indicating information is displayed as a low image-quality indicating image on the accessing-side client viewer 2, the low image-quality indicating image indicates a notice to the effect that that even if a user requests that an image is displayed in the same resolution as in images displayed by a monitor usually used by the user, there is a possibility from the specification of the accessing-side client viewer 2 that it could not be displayed in the above resolution, and the image quality may be lowered. To be more specific, if a user who usually observes a 512- by 512-pixel CT image with a monitor having 512- by 512-pixel resolution or more, now uses an accessing-side client viewer 2 including a monitor such as a PDA, which has a low resolution, to get access to the server 1, the monitor cannot display an image in 512- by 512-pixel resolution, and the image quality is lower than that of the image usually observed by the user. Thus, in this case, the accessing-side client viewer 2 is made to display the above notice for the user.

Then, the step to be carried out proceeds from the step Sa6 to the step Sa7. However, it should be noted that if it is determined in the step Sa5 that the above determined resolution and the resolution of the accessing-side client viewer 2 are approximately equivalent, the step to be carried out proceeds from the step Sa5 to Sa7. In the step Sa7, the image transmission section 104 reads medical image data specified by the image transmission request from the image storage section 103, and transmits it to the accessing-side client viewer 2.

In such a manner, when the first unreasonable state is detected in the processing in which medical image data is transmitted in response to the image transmission request from a client viewer 2, a notice to the effect that there is a possibility that the image quality may be lower than usual is indicated.

The checking for each of the second to fourth unreasonable states is carried out in response to an execution request which is given by the administrator by using the input device 112.

When execution of the checking for the second unreasonable state is requested, as shown in FIG. 6, use checking is carried out by the use-state monitoring section 106, the unreasonable state detecting section 109, and the solution plan preparing section 111.

In a step Sb1, the use-state monitoring section 106 analyzes the information stored in the use-state information storage section 105, to thereby collect the statistics of users and image transmission requests.

In a step Sb2, the use-state monitoring section 106 determines whether to carry out the checking for the second unreasonable state with reference to a user criterion or an image criterion. Specifying of one of these criterions is carried out, by the administrator, along with giving of an execution request for the checking the second unreasonable state. When the user criterion is specified, the step to be carried out by the use-state monitoring section 106 proceeds from the step Sb2 to the step Sb3. In the step Sb3, the use-state monitoring section 106 classifies the loads on the client viewers 2 into a low load, an appropriate load and an overload on the basis of which users frequently use the client viewers 2, respectively. To be more specific, in the case where a user who frequently uses a client viewer 2 is a person who observes images obtained in resolution lower than that of the monitor of the client viewer 2, the load on the client viewer 2 is classified as the low load. When a user who frequently uses a client viewer 2 is a person who observes images obtained in substantially the same resolution as the monitor of the client viewer 2, the load on the client viewer 2 is classified as the appropriate load. In the case where a user who frequently uses a client viewer 2 is a person who observes images obtained in resolution higher than that of the monitor of the client viewer 2, the load on the client viewer 2 is classified as the overload load. Furthermore, in the case where there is a client viewer 2 which is not frequently used by any of the users, the load on the client viewer 2 is classified as the low load. It should be noted that it can be estimated from, e.g., the type of the occupation of a user, what monitor is required by the user with respect to resolution. For example, a doctor who checks a medical image for diagnosis needs a monitor having high resolution, but a nurse has only to view a monitor having a relatively low resolution. Thus, a set table indicating a relationship between the types of occupations and resolutions of monitors is prepared and stored in the server 1.

On the other hand, when the image criterion is specified, the step to be carried out proceeds from the step Sb2 to the step Sb4. In the step Sb4, the use-state monitoring section 106 classifies the loads on the client viewers 2 into the low load, the appropriate load and the overload on the basis of medical images respectively frequently displayed on the client viewers 2. To be more specific, in the case where medical images frequently displayed on a client viewer 2 were obtained in resolution lower than that of the monitor of the client viewer 2, the load thereon is classified as the low load. In the case where medical images frequently displayed on a client viewer 2 were obtained in resolution which was substantially the same as that of the monitor of the client viewer 2, the load thereon is classified as the appropriate load. In the case where medical images frequently displayed on a client viewer 2 were obtained in resolution higher than that of the monitor of the client viewer 2, the load thereon is classified as the overload. In the case where a client viewer 2 hardly displays a medical image, the load on it is classified as the low load.

Then, the step to be carried out proceeds from the step Sb3 or the step Sb4 to the step Sb5. In the step Sb5, the unreasonable state detecting section 109 performs retrieval to detect a combination of a client viewer 2 the load on which is classified as the overload and a client viewer 2 the load on which is classified as the low load and the resolution of which is greater than that of the above client viewer 2 the load on which is classified as the overload. At this time, when the combination of the above client viewers 2 is detected, it means that they are in the second unreasonable state. Furthermore, in the case where there are a plurality of client viewers 2 the loads on which are each classified as the low load, one of these client viewers 2 is selected, which has resolution required to display an image to be displayed by a client viewer 2 the load on which is classified as the overload. If there is no client viewer 2 having the above required resolution, a client viewer 2 having resolution closest to the required resolution is selected.

In the step Sb6, the unreasonable state detecting section 109 determines whether the above combination has been detected or not. When it is determined in the step Sb6 that the combination has been detected, the step to be carried out proceeds from the step Sb6 to the step Sb7. In the step Sb7, the solution plan preparing section 111 prepares a suggestion image for changing the use state of client viewers 2, and makes the display device 113 display the suggestion image. As the suggestion image, the following image can be considered: an image which prompts the administrator to interchange the monitors of the combination of the client viewers 2 detected in the step Sb5 with each other, or an image which prompts one or some of users of client viewers 2 the loads on which are classified as the overload to use a client viewer or viewers 2 the loads on which are classified as the low load.

FIG. 7 is a view showing by way of example a situation in which it is determined that the second unreasonable state is detected with respect to the user criterion. In the situation shown in FIG. 7, the monitor of the client viewer 2-1 provided in a room A is lower than that of the monitor of the client viewer 2-2 provided in a room B. In addition, the client viewer 2-1 is frequently used by a user who needs a monitor having high resolution to check a medical image for diagnosis. The client viewer 2-2 is frequently used by a user who has only to refer to a medical image, and does not need a monitor having high resolution. In such a situation, by the display device 113 of the server 1, an image which suggests that the client viewers 2-1 and 2-2 be interchanged is displayed.

Figure 8A:
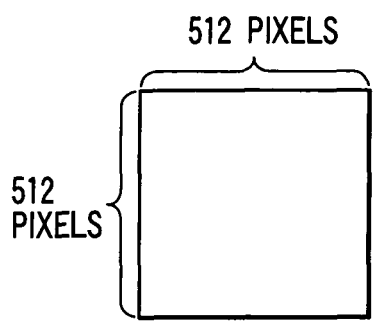
FIGS. 8A to 8D are views showing by way of example situations in each of which the unreasonable state is detected in the use checking.
Figure 8B:
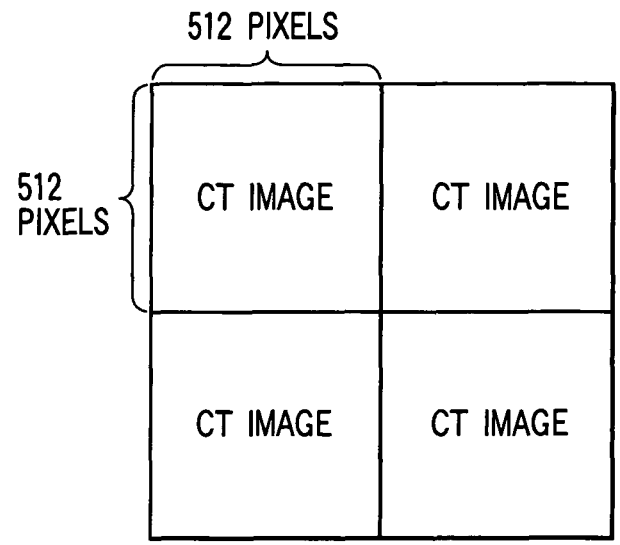
Figure 8C:
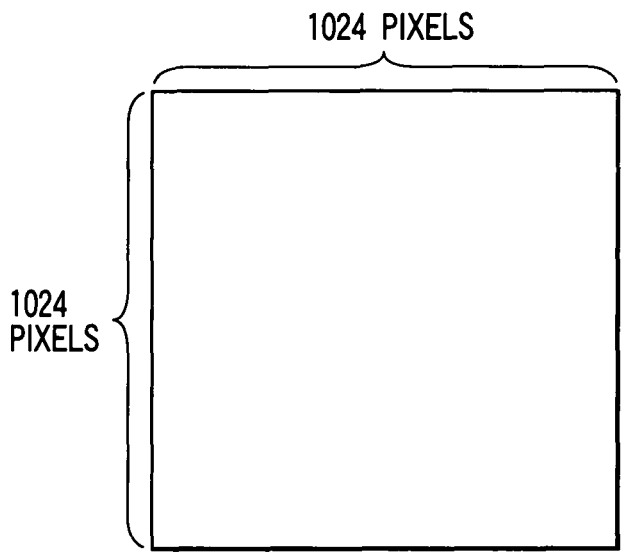
Figure 8D:
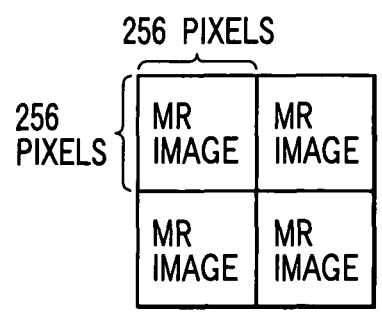

FIGS. 8A to 8D are views showing, by way of example, situations in each of which the second unreasonable state is detected in the checking with reference to the image criterion. In one of the situations, such a monitor having a 512- by 512-pixel resolution as shown in FIG. 8A is frequently used to display four 512- by 512-pixel CT images as shown in FIG. 8B. Furthermore, in the other situation, such a monitor having a 1024- by 1024-pixel resolution as shown in FIG. 8C is frequently used to display four 256- by 256-pixel MR images as shown in FIG. 8D. In those situations, by interchanging the above monitors, an optimal environment for checking CT images for diagnosis can be provided while satisfying a condition necessary for checking MR images for diagnosis. Thus, a suggestion image indicating interchanging of the monitors is displayed by the display device 113.

In the above example, the suggestion image to be displayed suggests that the monitors be interchanged with each other is displayed; however, it may suggest that the client viewer 2 to be used by users be changed to another one of the client viewer 2. Furthermore, the monitor of a client viewer 2 the load on which is classified as the appropriate load may be applied as a monitor with which one of the above monitors is to be interchanged or which other users are prompted to use.

It should be noted that there is a case where a user tends to observe the same types of images in the same arrangement. Therefore, when a user who has not yet used the medical image observing system gets access to it for the first time, the server 1 enables the user to select and use an appropriate client viewer 2, and can reduce the possibility that the second unreasonable state may occur, by performing the following processing: the server 1 requests the user to specify the type of each of images to be observed and the arrangement of the images; the server 1 calculates resolution necessary for displaying the images in the arrangement specified by the user, on the basis of the image type and arrangement specified by the user; and the server 1 makes a display section of a client viewer 2 used by the user display an image which indicates that the above selected client viewer 2 is an appropriate one for the user.

Figure 9:
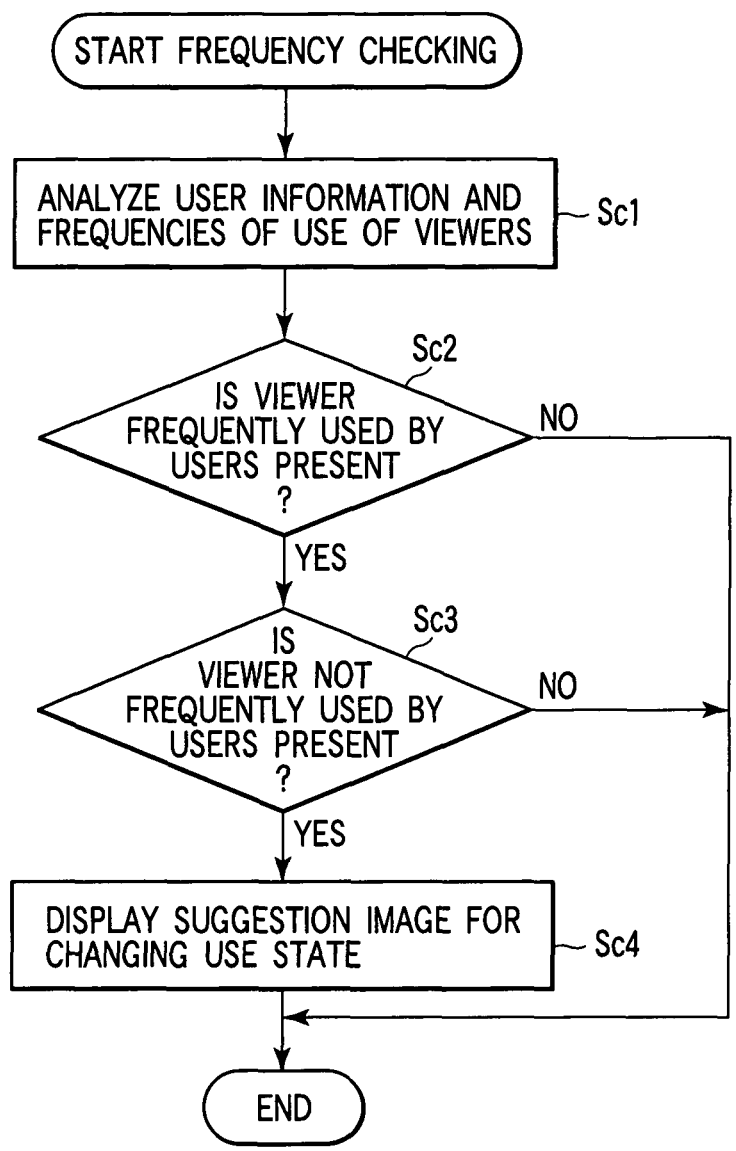
FIG. 9 is a flowchart of frequency checking.

Then, when a request for execution of checking for the third unreasonable state is given, the use-state monitoring section 106, the unreasonable state detecting section 109 and the solution plan preparing section 111 execute such frequency checking as shown in FIG. 9.

In the step Sc1, the use-state monitoring section 106 analyzes which users have used the client viewers 2, respectively, and the frequencies of use of the client viewers 2, on the basis of the information stored in the use-state information storage section 105.

In the steps Sc2 and Sc3, the unreasonable state detecting section 109 determines whether a client viewer 2 frequently used by a number of users is present or absent, and whether a client viewer 2 not frequently used by a number of users is present or absent. When it is determined that a client viewer 2 frequently used by a number of users is absent, and a client viewer 2 not frequently used by a number of user is also absent, or it is determined that one of a client viewer 2 frequently used by a number of users and a client viewer 2 not frequently used by a number of users is present, it is not detected that the third unreasonable state occurs, and thus the frequency checking ends.

On the other hand, when a client viewer 2 frequently used by a number of users and a client viewer 2 not frequently used by a number of users are both present, the frequencies of use of the client viewers 2 are unbalanced. It means that the third unreasonable state occurs. Thus, in this case, the solution plan preparing section 111 makes the display device 113 display a suggestion image for changing the use state. As the suggestion image, the following image can be considered: an image which prompts a user to move the client viewer 2 not frequently used to a room in which the client viewer 2 frequently used is provided, or an image which prompts one or some of the users of the client viewer 2 frequently used to use the client viewer 2 not frequently used.

Figure 10A:
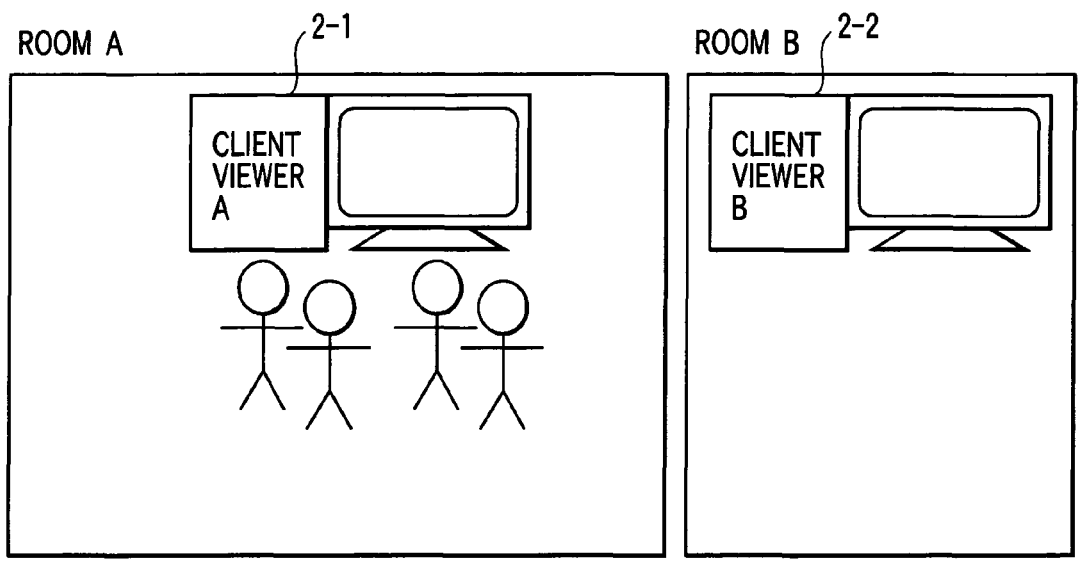
FIGS. 10A and 10B are views showing a situation in which an unreasonable state is detected in checking with respect to the frequency of use.
Figure 10B:
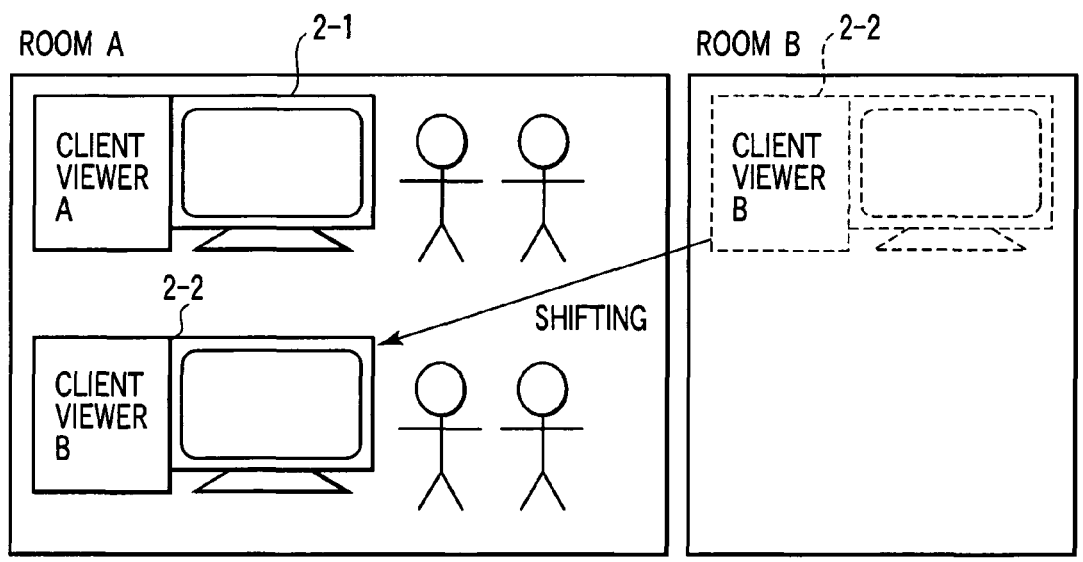

FIG. 10A is a view showing by way of example a situation in which the third unreasonable state is detected. In the situation shown in FIG. 10A, the client viewer 2-1 provided in the room A is frequently used by a number of users, but the client viewer 2-2 in the room B is not frequently used. In such a situation, the difference between the frequencies of use of the client viewers 2-1 and 2-2 can be reduced by moving the client viewer 2-2 to the room A as shown in FIG. 10B. Thus, an image which suggests that the client viewer 2-2 be shifted to the room A is displayed on the display device 113 of the server 1.

It should be noted that in the medical image observing system including a number of client viewers 2, there is a case where it is detected that a number of client viewers 2 not frequently used are present.

Figure 11A:
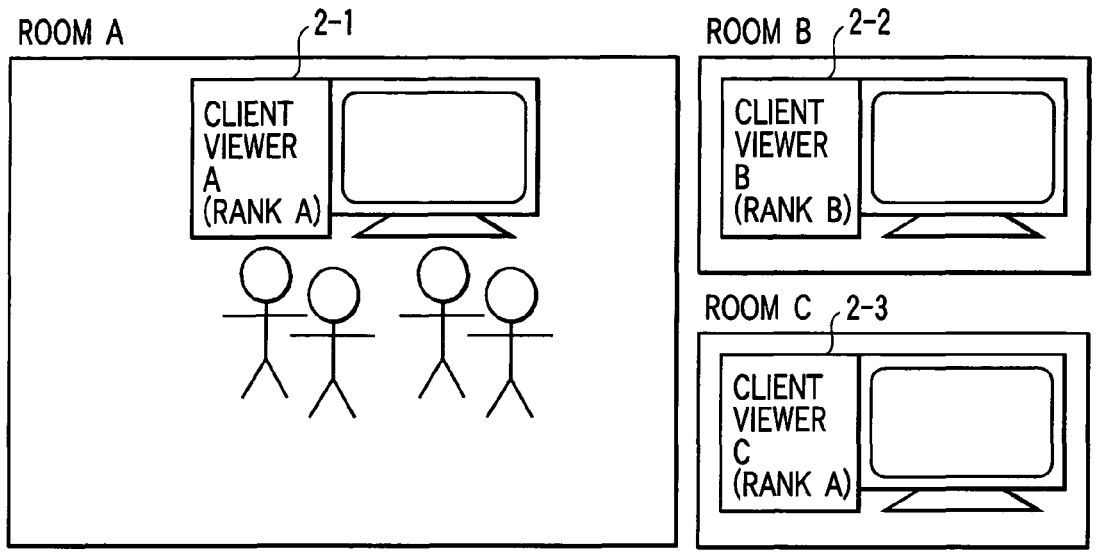
FIGS. 11A and 11B are views showing another situation in which the unreasonable state is detected in checking with respect to the frequency of use.

FIG. 11A is a view showing by way of example a situation in which the third unreasonable state is detected. In the situation shown in FIG. 11A, the client viewer 2-1 provided in the room A is frequently used by a number of users. On the other hand, neither the client viewer 2-2 in the room B nor the client viewer 2-3 in a room C is frequently used.

Figure 11B:
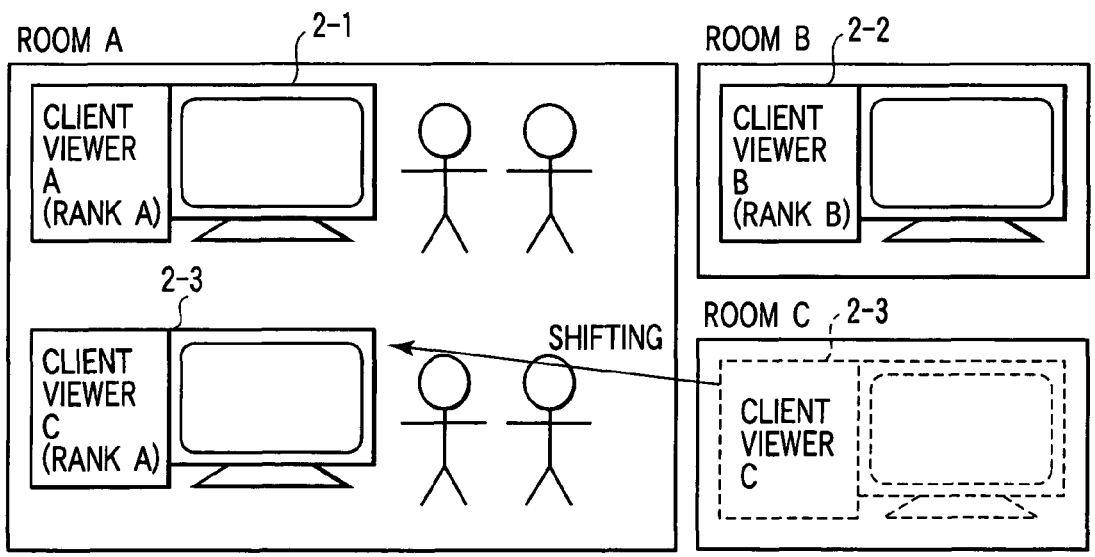

At this time, the display device 113 of the server 1 may be made to display an image which suggests that the client viewer 2-2 or 2-3 be shifted to the room A. Alternatively, the client viewer 2 to be shifted to the room A may be determined based on a predetermined condition. For example, if it is determined by referring to the specifications of client viewers 2, in the case shown in FIG. 11B, an image is displayed which suggests that the client viewer 2-3, whose function is equivalent to that of the client viewer 2-1, be shifted to the room A.

Figure 12:
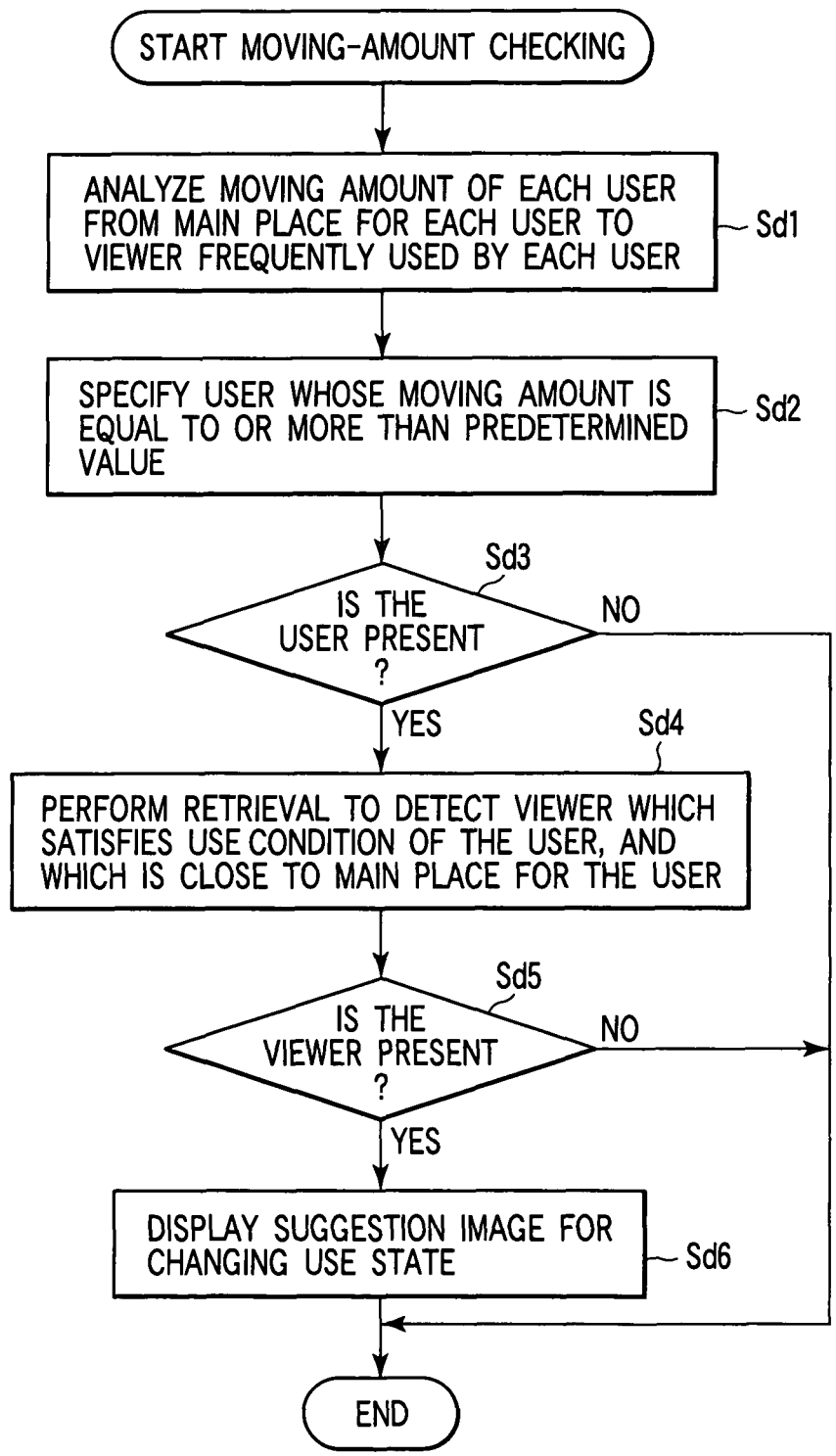
FIG. 12 is a flowchart of moving-amount checking.

When a request for execution of checking for the fourth unreasonable state is given, the use-state monitoring section 106, the unreasonable state detecting section 109 and the solution plan preparing section 111 execute such moving-amount checking as shown in FIG. 12.

Specifically, in a step Sd1, with respect to each of the client viewers 2, the use-state monitoring section 106 analyzes the moving amount of each of users which have already used each client viewer 2, from a main place for each user to each client viewer 2, on the basis of the information stored in the use-state information storage section 105. As the main place for each user, a place where each user is present at ordinary times is registered in advance. The moving amount can be estimated by referring to the information stored in the location information storage section 107 and the room arrangement information storage section 108.

In a step Sd2, the unreasonable state detecting section 109 specifies a user whose moving amount is equal to or more than a predetermined value, by referring to the result of the above analysis. Then, in a step Sd3, the unreasonable state detecting section 109 determines whether the user has been specified or not.

When it is determined in the step Sd3 that the above user has not been specified, it means that the fourth unreasonable state does not occur, and thus the moving-amount checking ends. On the other hand, it is determined in the step Sd4 that the user has been specified, the step to be carried out proceeds from the step Sb3 to a step Sb4. In the step Sb4, the unreasonable state detecting section 109 performs retrieval to detect a client viewer 2 which satisfies a use condition of the user which has been specified in the step Sb2, and which is located close to the main place for the user. Then, in a step Sb5, the unreasonable state detecting section 109 determines whether the above client viewer 2 has been detected or not.

It is determined in the step Sb5 that the client viewer 2 has not been detected, it means that the fourth unreasonable state does not occur, and thus the moving-amount checking ends. However, it is determined in the step Sb5 that the client viewer 2 has been detected, it means that the fourth unreasonable state occurs. In this case, the step to be carried out proceeds from the step Sb5 to a step Sb6. In the step Sb6, the solution plan preparing section 111 prepares a suggestion image for changing the use state, and makes the display device 113 display the suggestion image. As the suggestion image, an image can be considered which prompts the user the name of which has been retrieved in the step Sb2 to use the client viewer 2 detected in the step Sd4.

To be more specific, in the case where a number of client viewers 2 can provide equivalent environments for a diagnosis based on a medical image, if a user who makes the diagnosis uses one of the client viewers 2 which is far from the main place, it is not efficient. That is, it is more efficient that the user uses a client viewer 2 closer to the main place. Accordingly, by the display device 113 of the server 1, an image which suggests changing of the use state in order that the client viewer 2 closer to the main place be used.

However, it can be considered that a client viewer 2 far from the main place is intentionally used for any reason. For example, when the above user goes to another medical office, and then when he or she must urgently perform a diagnosis based on a medical image, there is a case where this state should not be determined as an unreasonable state. Furthermore, when a user uses a client viewer 2 far from his or her main place a number of times, there is a possibility that the user may intentionally use it, and there is thus also a case where this state should not be determined as an unreasonable state. Therefore, in the moving-amount checking also, the number of times a client viewer 2 has been used may be considered. For example, the step Sd2 may be carried out such that with respect to each client viewer 2, the unreasonable state detecting section 109 may specify only a user who uses it a number of times which is equal to a first threshold value or more, and is less than a second threshold value, as a result of which the above two states are not determined as the fourth unreasonable state.

As explained above, according to the first embodiment, it is detected whether each of the unreasonable states concerning use of the client viewers 2 occurs or not. Therefore, when it is detected that any of the unreasonable states occurs, e.g., the administrator of the medical image observing system can take measures for solving the problem of the detected unreasonable state, so that the medical image observing system can efficiently operate. Furthermore, according to the first embodiment, a plan for solving the problem of a detected unreasonable state is prepared and displayed. Thus the administrator does not need to consider what measures should be taken to solve the problem, thus further reducing the burden on the administrator.

Second Embodiment

The entire structure of a medical image observing system to which a computer system analyzing apparatus according to the second embodiment of the present invention is applied is substantially the same as that of the first embodiment. However, according to the second embodiment, a server 21 is used in place of the server 1.

Figure 13:
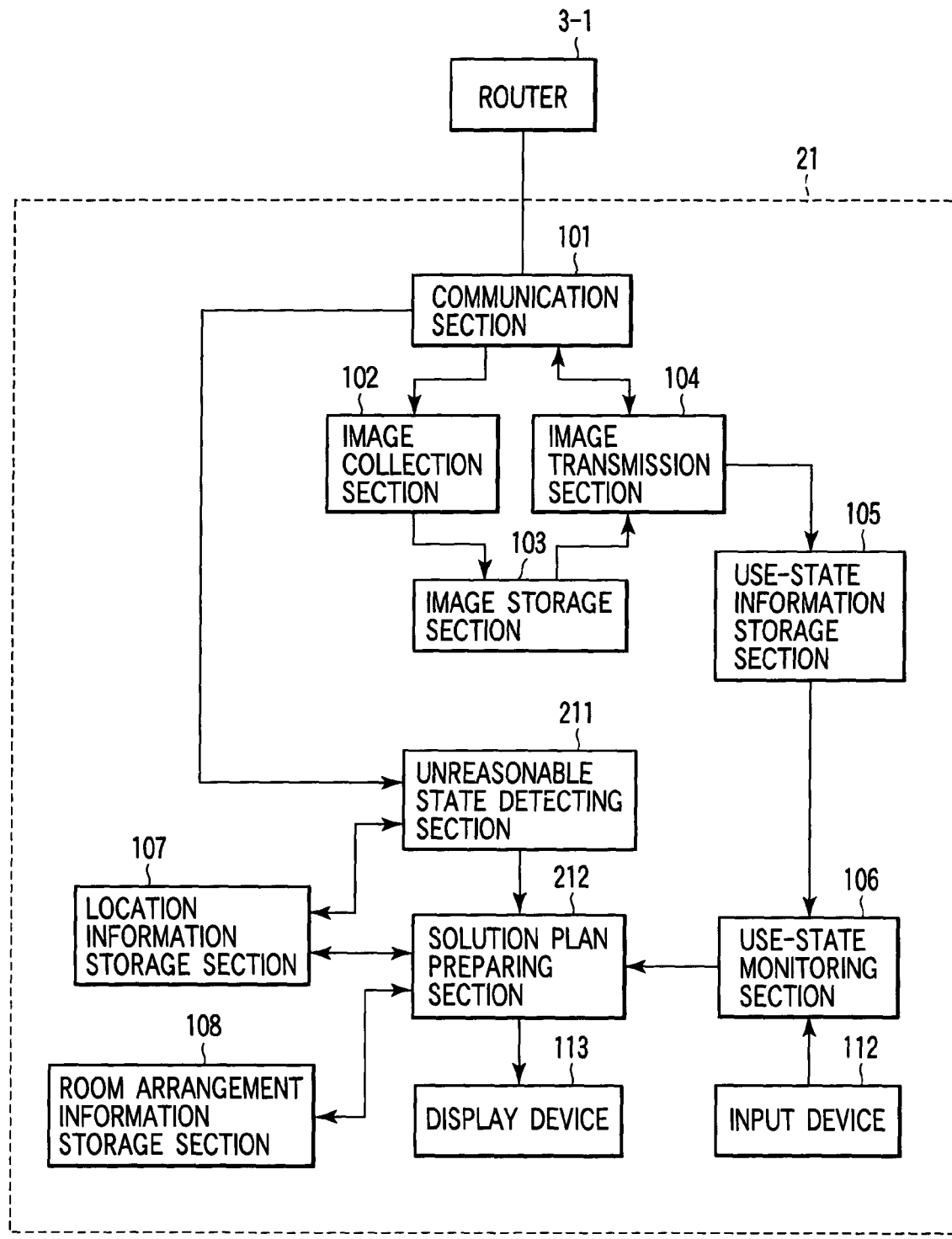
FIG. 13 is a block diagram showing the structure of a sever in a medical image observing system according to a second embodiment of the present invention.

FIG. 13 is a block diagram showing the structure of the sever 21. In FIG. 13, structural elements identical to those in the first embodiment will be denoted by the same reference numerals, respectively, and their detailed explanations will be omitted.

As shown in FIG. 13, the server 21 includes the communication section 101, the image collection section 102, the image storage section 103, the image transmission section 104, the use-state information storage section 105, the use-state monitoring section 106, the location information storage section 107, the room arrangement information storage section 108, the input device 112, the display device 113, an unreasonable state detecting section 211 and a solution plan preparing section 212.

The server 21 has no element corresponding to the low image-quality indicating section 110 in the sever 1. Furthermore, the sever 21 includes the unreasonable state detecting section 211 and the solution plan preparing section 212 in place of the unreasonable state detecting section 109 and the solution plan preparing section 111 in the server 1.

The unreasonable state detecting section 211 detects a state in which a user uses a client viewer 2 which is not suitable for the user, as an unreasonable state. When this unreasonable state is detected, the solution plan preparing section 212 prepares a plan for solving the problem of the unreasonable state.

To the location information storage section 107, data regarding the function of each of the client viewers 2 (e.g., the resolution of the monitor of each client viewer 2) is additionally written.

The operation of the medical image observing system having the above structure will be explained mainly with respect to the operation of the server 21.

Figure 14:
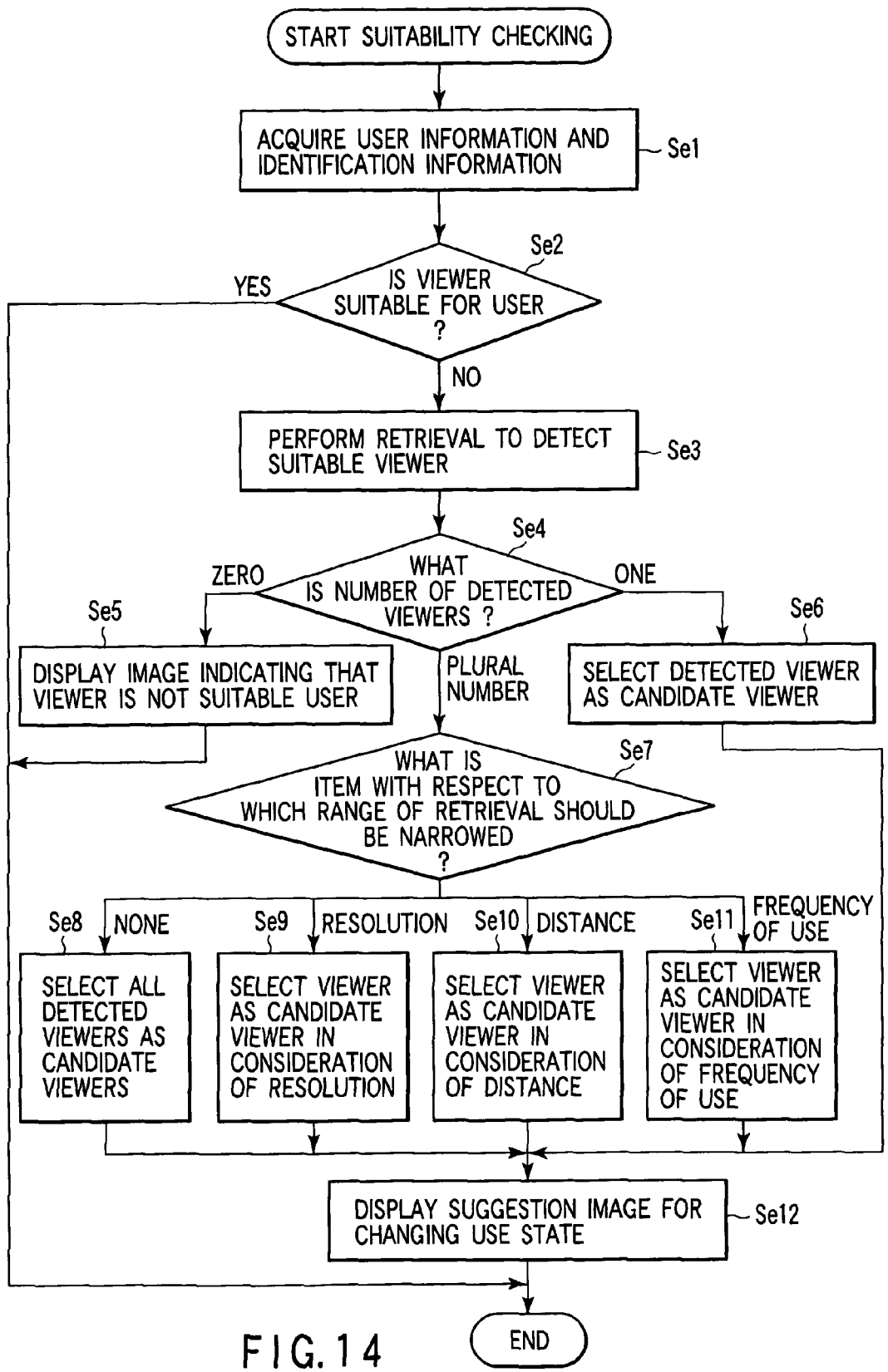
FIG. 14 is a flowchart of suitability checking.

When a user logs in on a client viewer 2 (where the user and the client viewer 2 will be hereinafter referred to as a logged-in user and a logged-in viewer 2, respectively), the logged-in viewer 2 transmits user information regarding the logged-in user and identification information regarding the logged-in viewer 2 to the server 21. When the user information and the identification information are received by the communication section 101, the unreasonable state detecting section 211 and the solution plan preparing section 212 execute such suitability checking as shown in FIG. 14.

Figures 15, 16:
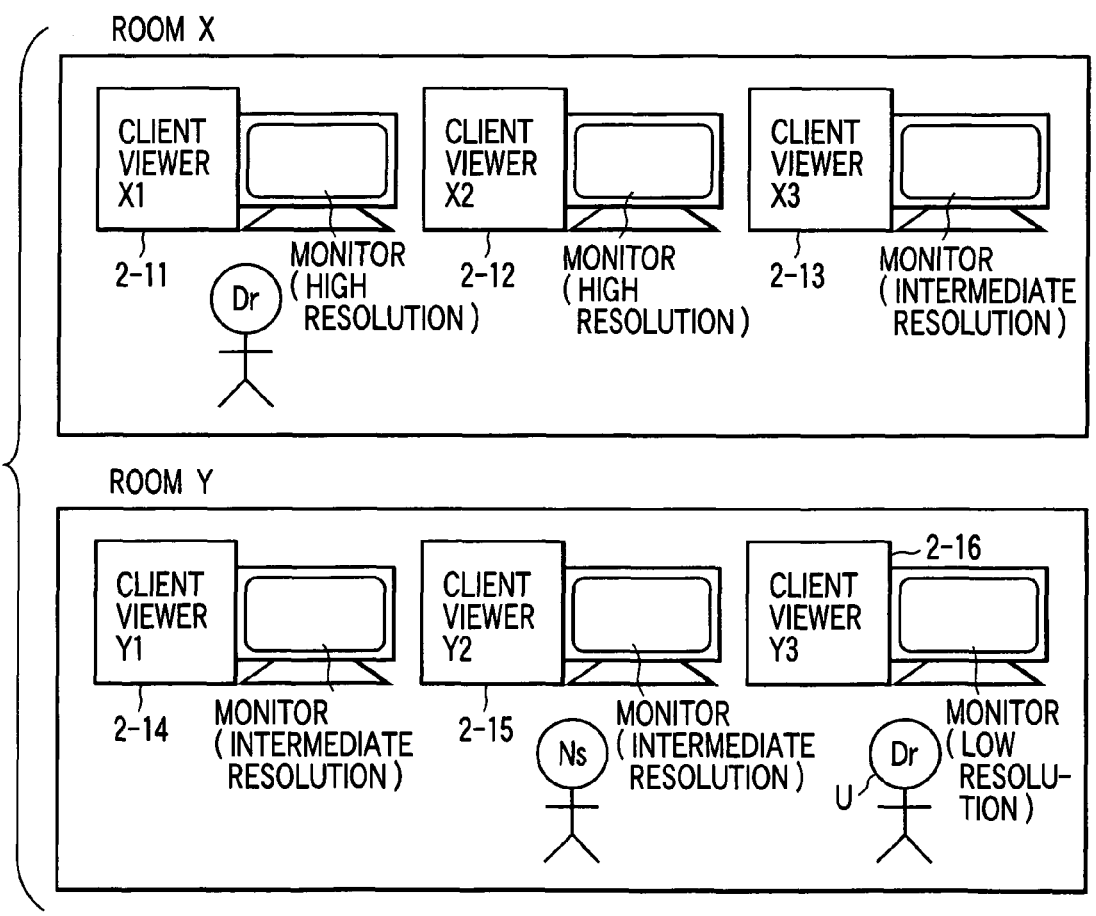
FIG. 15 shows a set table in which the types of monitors necessary for users are specified for the types of occupations of the users.
FIG. 16 is a view showing an example of an unreasonable state detected in the suitability checking.

Specifically, in a step Se1, the unreasonable state detecting section 211 acquires, from the communication section 101, the user information and identification information received thereby. In a step Se2, the unreasonable state detecting section 211 determines whether the logged-in viewer 2 is suitable for the logged-in user or not, on the basis of the user information and the identification information. Also, it can do so by referring to, e.g., such a set table as shown in FIG. 15. In the set table shown in FIG. 15, the types of monitors (classified with respect to resolution) necessary for users are specified for the types of occupations of the users. The set table is set by, e.g., the administrator. For example, if the logged-in user is a doctor, when the logged-in viewer 2 has a high-resolution monitor or an intermediate-resolution monitor, it is determined based on the above set table that the logged-in viewer 2 is suitable for the logged-in user, and when the logged-in viewer 2 has a low-resolution monitor, it is determined based on the set table that the logged-in viewer 2 is not suitable for the logged-in user. It should be noted that the type of the monitor included in the logged-in viewer 2 can be estimated by referring to the information stored in the location information storage section 107.

When it is determined in the step Se2 that the logged-in viewer 2 is suitable for the logged-in user, it is also determined that no unreasonable state occurs, and the suitability checking ends without carrying out the successive steps following the step Se2. On the other hand, when it is determined in the step Se2 that the logged-in viewer 2 is not suitable for the logged-in user, the step to be carried out proceeds from the step Se2 to a step Se3. In the step Se3, the solution plan preparing section 212 performs retrieval to detect a client viewer 2 suitable for the logged-in user, e.g., a client viewer 2 provided with a monitor which is suitable for the user with respect to the type of the monitor and the type of the occupation of the user.

In the step Se4, the solution plan preparing section 212 checks the number of client viewers 2 detected in the above retrieval, i.e., the number of times client viewers 2 have been detected. When the number is zero, the step to be carried out proceeds from the step Se4 to a step Se5. In the step Se5, the solution plan preparing section 212 makes the display device 113 display an image which indicates that the logged-in viewer 2 is not suitable for the logged-in user. This image is intended to indicate that using of the logged-in viewer 2 by the logged-in user is unreasonable. That is, it indicates only occurrence of an unreasonable state, since a substitute monitor to be used to solve the problem of the unreasonable state cannot be detected.

When the number of client viewers 2 detected in the retrieval is one, the step to be carried proceeds from the step Se4 to a step Se6. In the step Se6, the solution plan preparing section 212 selects the detected client viewer 2 as a candidate viewer.

When the number of client viewers detected in the retrieval is a plural number, the step to be carried out proceeds from the step Se4 to a step Se7. In the step Se7, the solution plan preparing section 212 refers to an item with respect to which the range of retrieval for detecting a suitable client viewer 2 should be narrowed. As the item, one of "resolution", "distance", "frequency of use" and "none" is selected in advance, by, e.g., the administrator.

When "none" is set, the step to be carried out proceeds from the step Se7 to a step Se8. In the step Se8, the solution plan preparing section 212 selects all the client viewers 2 detected in the retrieval, as candidate viewers. That is, at this time, narrowing of the range of the above retrieval is not carried out.

When "resolution" is set as the item, the step to be carried out proceeds from the step Se7 to a step Se9. In the step Se9, the solution plan preparing section 212 selects one or ones of the detected client viewers 2 as a candidate viewer or viewers in consideration of resolution. To be more specific, of the detected client viewers 2, a client viewer or viewers 2 provided with monitors having the highest resolution are selected as a candidate viewer or viewers.

When "distance" is set as the item, the step to be carried out proceeds from the step Se7 to a step Se10. In the step Se10, the solution plan preparing section 212 selects one or ones of the detected client viewers as a candidate viewer or viewers in consideration of the distance between each detected client viewer and the logged-in viewer 2. To be more specific, of the detected client viewers 2, a client viewer or viewers 2 located closest from the logged-in viewer 2 are selected as a candidate viewer or viewers.

When "frequency of use" is set as the item, the step to be carried out proceeds from the step Se7 to a step Se11. In the step Se11, the solution plan preparing section 212 selects one or ones of the detected client viewers 2 as a candidate viewer or viewers in consideration of the frequency of use of each detected client viewer 2. To be more specific, of the detected client viewers 2, a client viewer or viewers 2 which are the lowest with respect to the frequency of use are selected as a candidate viewer or viewers.

In any of the steps Se6 and Se8 to Se11, after a client viewer or viewers 2 are selected as a candidate viewer or viewers, the step to be carried out proceeds from said any of those steps to a step Se12. In the step Se12, the solution plan preparing section 212 prepares a suggestion image for changing the use state, and makes the display device 113 display the suggestion image. As the suggestion image, the following image can be considered: an image which prompts the administrator to interchange the monitor of the logged-in viewer 2 and that of the candidate viewer with each other, or an image which prompts the logged-in user to use the candidate viewer.

FIG. 16 is a view showing an example of a situation in which an unreasonable state is detected. The following is the situation shown in FIG. 16:

As shown in the figure, client viewers 2-11, 2-12 and 2-13 are provided in a room X, and client viewers 2-14, 2-15 and 2-16 are provided in a room Y. The client viewers 2-11 and 2-12 include respective high-resolution monitors. The client viewers 2-13, 2-14 and 2-15 include respective intermediate-resolution monitors. The client viewer 2-16 includes a low-resolution monitor. The client viewer 2-11 is frequently used by a doctor. The client viewer 2-15 is frequently used by a nurse. The client viewers 2-12, 2-13 and 2-14 are not frequently used.

In the above situation, suppose a user U who is a doctor logs in on the client viewer 2-16. According to the table shown in FIG. 15, a high-resolution monitor or an intermediate-resolution monitor is suitable for a doctor. Accordingly, the client viewer 2-16 is not suitable for the user U, since its monitor has low resolution.

At this time, the client viewers 2-11, 2-12, 2-13, 2-14 and 2-15 are detected as suitable viewers, i.e., candidate viewers, since they include high-resolution or intermediate-resolution monitors, which are suitable for the user U. Then, when "none" is set as the item, a suggestion image which lists the client viewers 2-11, 2-12, 2-13, 2-14 and 2-15 as candidate viewers is displayed. When "resolution" is set as the item, the candidate viewers are narrowed down to the client viewers 2-11 and 2-12 provided with the high-resolution monitors. When "distance" is set as the item, the candidate viewers are narrowed down to the client viewers 2-14 and 2-15 which are located in the same room as the client viewer 2-16.

Figures 17, 18:
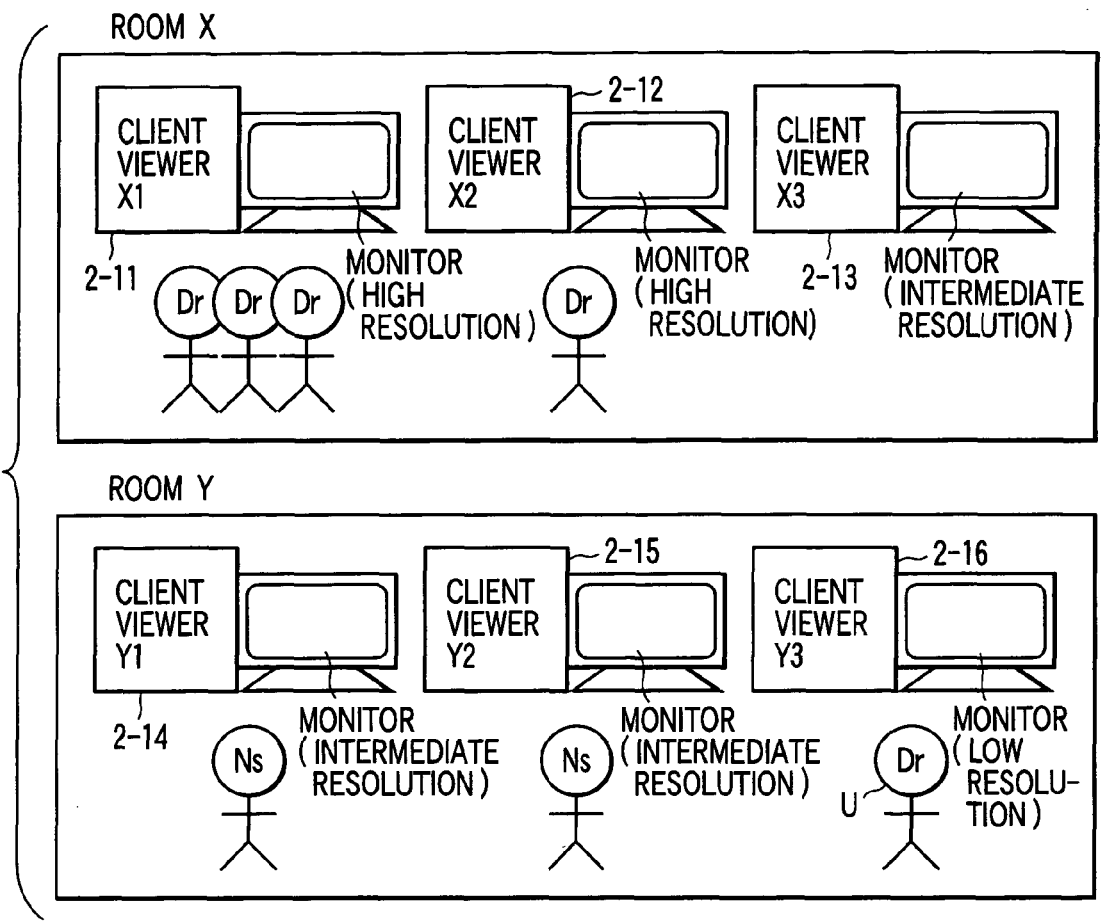
FIG. 17 is a view showing another example of the unreasonable state detected in the suitability checking.
FIG. 18 is a view showing an example of scores for use in narrowing candidate viewers.

It should be noted that the solution plan preparing section 212 may narrow the candidate viewers based on a number of items. This will be explained by way of example as follows:

In a situation shown in FIG. 17, the frequency of use of the client viewer 2-11 is high, those of the client viewers 2-12, 2-14, 2-15 and 2-16 are approximately intermediate, and that of the client viewer 2-13 is low.

In this situation, suppose the user U who is a doctor as stated above logs in on the client viewer 2-16. In this case, as shown in FIG. 18, the solution plan preparing section 212 determines the scores of all the client viewers including the client viewer 2-16 with respect to the resolution, the frequency of use and the distance between each client viewer and the client viewer 2-16. In the example shown in FIG. 18, with respect to each of the above three items, the client viewers are scored points at three levels, i.e., 9 points, 5 points and 1 point. Then, the solution plan preparing section 212 weights a coefficient set for each item to the score of each client viewer with respect to each item, and calculates the total score of each client viewer with respect to the three items. In the example in FIG. 18, the coefficients of the resolution, the frequency of use and the distance are 3, 2, 1, respectively. Then, the solution plan preparing section 212 selects a client viewer 2 the total score of which is the highest, as a candidate viewer. Alternatively, it may be set to select a number of client viewers 2 which are higher-ranked with respect to the total score.

In such a manner, according to the second embodiment, when a number of candidate viewers are present, they are narrowed down to a more suitable one or ones based on their attributes, and an image which suggests that the more suitable candidate viewer or viewers be used is displayed. As a result, the burden on the administrator is reduced.

The above embodiments can be variously modified as follows:

The present invention can be applied to various computer systems other than the medical image observing system. Furthermore, it can be applied to checking of computer resources other than the monitor, such as a computer and an external memory device. It should be noted that the computer resources include various devices which are necessary when the computer operates, such as a memory device, an input device, an output device, and a control device.

The checking may be carried out to detect only one or some of the first to fourth unreasonable states. Alternatively, it may be performed to detect another unreasonable state.

In the medical image observing system, an independent server for maintenance may be provided to have a function of performing checking for the unreasonable states. Alternatively, an external terminal such as the maintenance terminal 11, which is provided outside the medical image observing system, may be provided to have a function of performing checking for the unreasonable states. In the latter case, a number of medical image observing systems can share only one external terminal to perform checking.

Instead of the image which provides a plan for solving the problem of an unreasonable state, an image which indicates that an unreasonable state occurs may be displayed.

The image which provides a plan for solving the problem of an unreasonable state or the image which indicates that an unreasonable state occurs may be displayed by the monitor of a client viewer in which the unreasonable state occurs.

The function of a client viewer necessary for a user may be estimated based on attribute information other than the identification information regarding the user or the type of the occupation of the user (e.g., the level of the skill of the user).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A computer system analyzing apparatus comprising:
   a storage section;
   a unit which generates historical information by storing user information and monitor information in the storage section in association with each other every time a user observes a medical image by use of one of monitors that display the medical image, the user information indicating the user observing the medical image, the monitor information indicating one of the monitors that displays the medical images, wherein based on the historical information, a history of use of the monitors by the user is determinable;
   a unit which determines one of the monitors, which is being used by the user, as a currently used monitor;
   a determining unit which determines a monitor which is ordinarily used by the user by analyzing the historical information stored in the storage section, as an ordinarily used monitor;
   a detecting unit which detects, as an unreasonable state, a state in which a resolution of the currently used monitor is lower than a resolution of the ordinarily used monitor; and
   an informing unit which informs the user that there is a possibility that processing which is performed by the currently used monitor could not be performed, when the detecting unit detects the unreasonable state.

2. The computer system analyzing apparatus according to claim 1, further comprising:
   a warning unit which operates when the detecting unit detects the unreasonable state and which warns the user that a display image of the currently used monitor is lower in quality than a display image of the ordinarily used monitor.

3. A computer system analyzing method comprising:
   generating historical information by storing user information and monitor information in a storage section in association with each other every time a user observes a medical image by use of one of monitors that display the medical image, the user information indicating the user observing the medical image, the monitor information indicating one of the monitors that display the medical images, wherein based on the historical information, a history of use of the monitors by the user is determinable;
   determining one of the monitors, which is being used by the user, as a currently used monitor;
   determining a monitor which is ordinarily used by the users by analyzing the historical information stored in the storage section, as an ordinarily used monitor;
   detecting, as an unreasonable state, a state in which a resolution of the currently used monitor is lower than a resolution of the ordinarily used monitor; and
   informing the user that there is a possibility that processing which is performed by the currently used monitor could not be performed, when the unreasonable state is detected.

* * * * *